(12) United States Patent
Ben Shoshan et al.

(10) Patent No.: US 10,799,147 B2
(45) Date of Patent: Oct. 13, 2020

(54) MAGNETIC PICKUP CANCELLATION BY COMPENSATION LEADS

(71) Applicant: BIOSENSE WEBSTER (ISRAEL) LTD., Yokneam (IL)

(72) Inventors: Sharona Ben Shoshan, Zichron Yaacov (IL); Eden Kidishman, Modiin (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 361 days.

(21) Appl. No.: 16/018,614

(22) Filed: Jun. 26, 2018

(65) Prior Publication Data

US 2019/0388003 A1    Dec. 26, 2019

(51) Int. Cl.

| | |
|---|---|
| *G01R 33/00* | (2006.01) |
| *A61B 5/06* | (2006.01) |
| *A61B 34/20* | (2016.01) |
| *G01V 3/10* | (2006.01) |
| *H05K 1/02* | (2006.01) |

(52) U.S. Cl.
CPC .............. *A61B 5/062* (2013.01); *A61B 34/20* (2016.02); *G01V 3/10* (2013.01); *H05K 1/028* (2013.01); *H05K 1/0228* (2013.01); *A61B 2034/2051* (2016.02); *A61B 2562/0223* (2013.01); *A61B 2562/182* (2013.01); *H05K 2201/10151* (2013.01)

(58) Field of Classification Search
CPC .. G01R 33/0017; G01R 33/025; A61B 5/062; A61B 2562/0223; H05K 1/0228; H05K 2201/10151

USPC ........................................................ 174/250
See application file for complete search history.

(56) References Cited

U.S. PATENT DOCUMENTS

| | | | |
|---|---|---|---|
| 5,357,050 A | * | 10/1994 | Baran ................. H05K 1/0228 174/261 |
| 5,391,199 A | | 2/1995 | Ben-Haim |
| 6,073,043 A | | 6/2000 | Schneider |
| 6,239,724 B1 | | 5/2001 | Doron et al. |
| 6,263,229 B1 | | 7/2001 | Atalar et al. |
| 6,332,089 B1 | | 12/2001 | Acker et al. |
| 6,484,118 B1 | | 11/2002 | Govari |

(Continued)

FOREIGN PATENT DOCUMENTS

| | | |
|---|---|---|
| WO | WO 1996/05768 A1 | 2/1996 |
| WO | WO 2017/136599 A1 | 8/2017 |

OTHER PUBLICATIONS

European Search Report for corresponding EPA No. 19182284.0 dated Nov. 6, 2019.

(Continued)

*Primary Examiner* — Sherman Ng

(57) ABSTRACT

A wiring assembly includes a differential input port, a differential output port, and first and second pairs of electrical leads. The differential input port is configured to receive a differential signal from a sensor at a first end of the wiring assembly. The differential output port is configured to output the differential signal at a second end of the wiring assembly. The first and second pairs of electrical leads convey the differential signal from the first end to the second end, and are connected to one another at the first end and at the second end in a configuration that cancels pickup of an ambient magnetic field by the wiring assembly.

10 Claims, 3 Drawing Sheets

(56) References Cited

U.S. PATENT DOCUMENTS

| | | |
|---|---|---|
| 6,618,612 B1 | 9/2003 | Acker et al. |
| 6,690,963 B2 | 2/2004 | Ben-Haim et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2010/0312096 A1 | 12/2010 | Guttman et al. |
| 2014/0039302 A1* | 2/2014 | Miller .................... H01R 24/86 600/424 |
| 2017/0014112 A1 | 1/2017 | Miller et al. |
| 2017/0273171 A1* | 9/2017 | Codd ................... H04N 5/2257 |

OTHER PUBLICATIONS

Steven Lampen, "How Starquad Works", Retrieved from the internet: URL:https://www.belden.com/blog/broadcast/how-starquad-works, Aug. 2, 2012.

\* cited by examiner

US 10,799,147 B2

MAGNETIC PICKUP CANCELLATION BY COMPENSATION LEADS

FIELD OF THE INVENTION

The present invention relates generally improvements in sensor wiring schemes, and particularly to wiring schemes for reducing magnetic pickup in magnetic position-tracking systems.

BACKGROUND OF THE INVENTION

Various techniques were proposed for improving intra-body magnetic position sensors and their integration. For example, PCT International Application Publication WO 2017/136599 describes a medical device assembly for use in a magnetic environment, including a medical device comprising a shaft having proximal and distal end portions. The device further comprises a position sensor at the distal end portion of the shaft that comprises first and second leads extending therefrom to the proximal end portion of the shaft. The device further comprises an electromechanical connector having a plurality of connection points at a first end thereof. First and second of the connection points are electrically connected to the first and second sensor leads, respectively. The connector further comprises an error loop segment electrically coupled to third and fourth connection points. The error loops segment assists in forming a compensation loop that can be used to correct for magnetic noise.

As another example, U.S. Pat. No. 6,073,043 describes a method and apparatus for determining the position and orientation of a remote object relative to a reference coordinate frame. The apparatus can be used for locating the end of a catheter or endoscope, digitizing objects for computer databases, virtual reality and motion tracking. The apparatus includes a plurality of field-generating elements for generating electromagnetic fields, a drive for applying, to the generating elements, signals that generate a plurality of electromagnetic fields that are distinguishable from one another, a remote sensor having one or more field-sensing elements for sensing the fields generated and a processor for processing the outputs of the sensing element (s) into remote object position and orientation relative to the generating element reference coordinate frame. The methods presented here can also be applied to other magnetic tracking technologies as a final "polishing" stage to improve the accuracy of their position and orientation solution In another field, U.S. Pat. No. 6,263,229 describes several embodiments of methods of making magnetic resonance catheter coils. At least one par of generally parallel electrically conductive coil elements, which are electrical connected to each other, is patterned on a flexible electrically insulative base member. A catheter is provided over the coil assembly. In one embodiment, a second pair of generally parallel electrically conductive coil elements are provided in order to create a quadrature coil. In some embodiments, tuning and matching circuits and decoupling circuits may be provided. The (a) coils, (b) coil assemblies, as well as (c) catheter coils containing coil assemblies produced by these methods are also disclosed. The coils may be miniaturized so as to facilitate ready insertion within a suitable sheath, such as a probe or catheter, into a patient, including into body openings, or into blood vessels or into interior regions of the body.

SUMMARY OF THE INVENTION

An embodiment of the present invention provides a wiring assembly including a differential input port, a differential output port, and first and second pairs of electrical leads. The differential input port is configured to receive a differential signal from a sensor at a first end of the wiring assembly. The differential output port is configured to output the differential signal at a second end of the wiring assembly. The first and second pairs of electrical leads convey the differential signal from the first end to the second end, and are connected to one another at the first end and at the second end in a configuration that cancels pickup of an ambient magnetic field by the wiring assembly.

In some embodiments, the wiring assembly further includes readout circuitry, which is coupled to receive the outputted differential signal at the second end of the wiring assembly.

In some embodiments, the first pair of leads and the second pair of leads encompass a same area, up to a preset tolerance.

In an embodiment, the second pair of leads is inverse-parallel connected to the first pair of leads.

In another embodiment, the second pair of leads is connected in series to the first pair of leads.

In some embodiments, the first pair of leads and the second pair of leads are patterned on a flexible printed circuit board (PCB).

In some embodiments, the sensor includes a magnetic sensor.

There is additionally provided, in accordance with an embodiment of the present invention, an assembly wiring method, including providing a differential input port, configured to receive a differential signal from a sensor at a first end of a wiring assembly. A differential output port, which is configured to output the differential signal at a second end of the wiring assembly, is also provided. A first pair of electrical leads and a second pair of electrical leads are wired to create the wiring assembly, such that the first pair of leads and the second pair of leads are wired to each other in a configuration that cancels interfering signals picked up by the first and second pairs due to an ambient magnetic field.

The present invention will be more fully understood from the following detailed description of the embodiments thereof, taken together with the drawings in which:

DETAILED DESCRIPTION OF EMBODIMENTS

Overview

Figure 1:
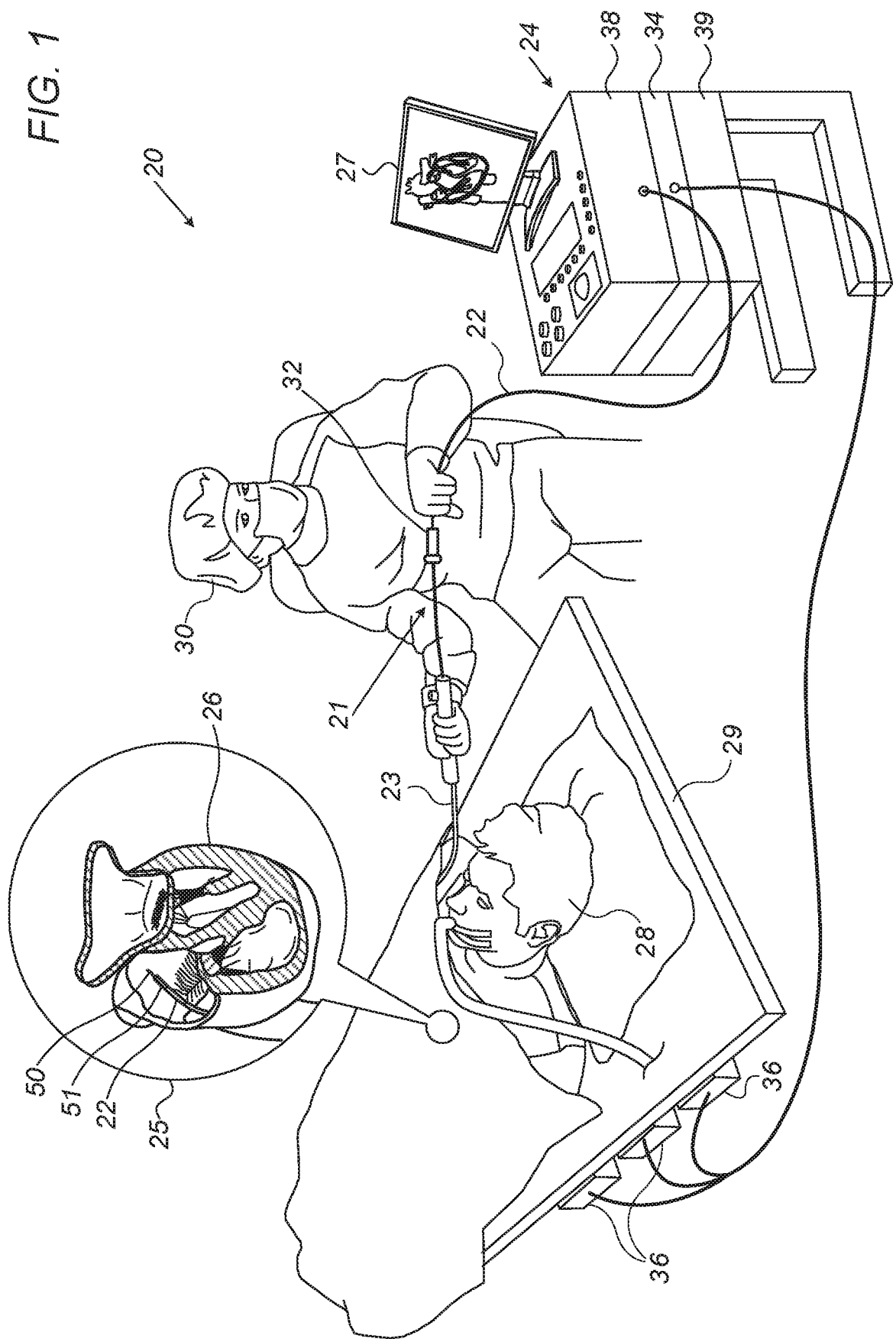
FIG. 1 is a schematic, pictorial illustration of a catheter-based magnetic position-tracking and ablation system, in accordance with an embodiment of the present invention.

Embodiments of the present invention that are described herein provide improved assembly wiring methods and wiring assemblies for reducing interference that is picked-up by electrical wiring in a magnetic field. The embodiments described herein refer mainly to wiring that runs through a catheter, from a sensor at the distal end of the catheter to readout circuitry at the proximal end. The disclosed assembly wiring techniques, however, are applicable in various other systems and applications.

In some embodiments, coil sensor included in a catheter-based position-tracking system generates differential signals in response to an alternating magnetic field. The signals are transmitted to a differential input port at a first end of a wiring, assembly, and then conveyed by the wiring assembly to a differential output port at a second end of the wiring assembly. In some embodiments, an amplifier is coupled to receive the outputted differential signal at the second end of the wiring assembly.

In general, a wiring assembly may generate interfering electric potentials, for example, in response to alternating magnetic fields traversing an area encompassed by a pair of leads included in the assembly (the pair essentially acting as a single winding coil having a non-zero area). The interfering signals may distort the sensor signals and degrade the overall performance of a system using the signals, such as in a catheter-based position-tracking system using position signals generated by a magnetic sensor.

Embodiments of the present invention that are described hereinafter provide wiring configurations in which a first and second pairs of electrical leads, which convey the differential signal from a first end to a second end, and which are connected to one another at the first end and at the second end in a configuration that cancels pickup of an ambient magnetic field by the wiring assembly. As noted above, such wiring assembly can be used, for example to connect a sensor to electrical readout circuitry.

In some embodiments, the wiring assembly comprises a first pair of leads that is connected to a coil of a magnetic sensor. The first pair of leads may pick up interfering signals from ambient magnetic fields traversing an area encompassed by the leads. A second pair of leads of the wiring assembly, having a similar geometrical arrangement as the first pair (e.g., encompassing a same area, up to a pre-defined tolerance), is connected in an inverse-parallel configuration to the first pair of leads in order to compensate for an interfering signal generated by the first lead pair.

In the disclosed inverse-parallel connection configuration, the two pairs of leads are connected in parallel, but with their polarities reversed, as further described below. An interfering signal generated by the second lead pair is essentially the same as the interfering signal generated by the first lead pair, but with inverse polarity, and thus can be used to cancel the interfering signal inputted to readout circuitry. The two pairs of leads (i.e., four leads) are reduced by the disclosed wiring configurations into two leads that feed sensor signals to readout circuitry, such as comprising a single amplifier, with the interfering signals canceled already at the input of the amplifier.

In some embodiments, the wiring assembly comprises a first lead pair and a second lead pair, which are connected in series to feed a single amplifier. To compensate for the interfering signal generated by the first pair, the second pair of leads, having a similar geometrical arrangement as the first pair, is incorporated, in series, in a way that cancels out the induced interfering signals at the input of the amplifier. Again, an interfering signal generated in the second lead pair is essentially the same as the interfering signal generated by the first lead pair, but of inverse polarity, so an interconnection of the two pairs of leads in series cancels the interfering signals.

Heuristically, the disclosed inverse-parallel connection configuration can be treated as cancelling interfering voltages, and the in-series connection configuration can be treated as cancelling interfering currents. A particular selection of one of the two connecting schemes may depend on details of the readout circuitry, such as amplifier type.

In some embodiments, a flexible printed circuit board (PCB) is patterned with the two pairs of leads. The two pairs of leads are patterned such that the first pair and the second pair are either connected with an inverse-parallel configuration, or an in series configuration, to feed a single amplifier. In other embodiments, the disclosed connection schemes are used to couple one or more sensors to readout circuitry comprising multiple amplifiers. Such multiple-amplifier circuitry is typically fed by numerous signals, that require the disclosed pickup noise cancellation schemes, as would occur to a person skilled in the art.

The disclosed wiring configurations for the cancellation of magnetic pickup noise to avoid inputting to readout circuitry pick up noise with the signal result in higher quality output signals from readout circuitry when compared to using bulky solutions, such as "twisted-pair" insulated wires. By patterning the leads on a PCB, the disclosed techniques may be advantageous for compact electrical layouts, as is required for fitting multiple sensors at the distal end of a catheter. The disclosed lead architectures and patterning techniques may thus allow better miniaturization, as well as cost-effectiveness, of instruments such as catheters.

The disclosed technique is further advantageous over less compact solutions (e.g., twisted-pairs), as the disclosed embodiments are especially adapted for high-frequency alternating magnetic fields, in which the "twist pitch" of wires must be tight enough to ensure low pickup noise. Twisting the leads sufficiently thus becomes a demanding and expensive process, while the disclosed patterning techniques conforms more readily with such requirements.

System Description

FIG. 1 is a schematic, pictorial illustration of a catheter-based magnetic position-tracking and ablation system 20, in accordance with an embodiment of the present invention. System 20 comprises a catheter 21, having a shaft distal end 22 that is navigated by a physician 30 into a heart 26 of a patient 28 via the vascular system. In the pictured example, physician 30 inserts shaft distal end 22 through a sheath 23, while manipulating the distal end of shaft distal end 22 using a manipulator 32 near the proximal end of the catheter. As shown in an inset 25, shaft distal end 22 comprises a magnetic sensor 51 contained within the shaft distal end 22 and an ablation catheter 50.

In the embodiments described herein, catheter 21 is used for ablation of tissue in heart 26. Although the pictured embodiment relates specifically to the use of ablation catheter 50 for ablation or heart tissue, the elements of system 20 and the methods described herein may alternatively be applied in position-tracking of other catheter types, such as electrophysiological mapping catheters. Moreover, the disclosed assembly wiring techniques may be used to improve signal quality received from other sensors fitted at distal end 22, such as contact force sensors and electrophysiological activity sensors.

The proximal end of catheter 21 is connected to a control console 24. Console 24 comprises a processor 39, typically a general-purpose computer, with suitable front end and interface circuits 38 for receiving signals from catheter 21, as well as for applying energy via catheter 21 to ablate tissue in heart 26 and for controlling the other components of system 20. Console 24 also comprises a driver circuit 34, configured to drive magnetic field generators 36.

During a navigation of shaft distal end 22 in heart 26, console 24 receives signals from magnetic sensor 51 in response to magnetic fields from external field generators 36, for example, for the purpose of measuring the position of ablation catheter 50 in the heart and, optionally, presenting the tracked position on a display 27. Magnetic field generators 36 are placed at known positions external to patient 28, e.g., below a patient table 29. These position signals are indicative of the position of ablation catheter 50 in the coordinate system of the position-tracking system. In some embodiments, the wiring assembly (not shown) that conveys the signals from sensor 51 to console 24 is configured to, according one of the disclosed assembly wiring methods, cancel pickup noises due to the magnetic fields irradiated from generators 36.

This method of position sensing using external magnetic fields is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 39 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Magnetic Pickup Cancellation by Compensation Leads

Figure 2A:
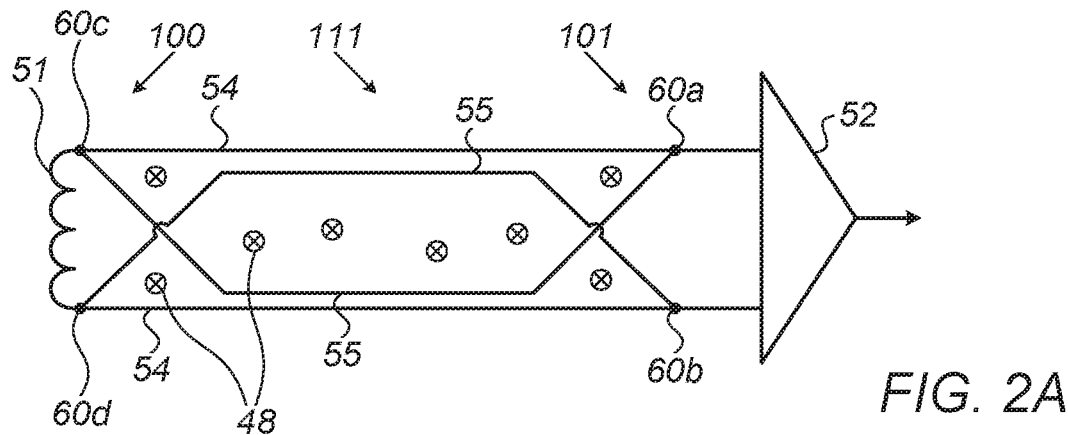
FIGS. 2A and 2B are schematic block diagrams of wiring assemblies configured to cancel magnetic pickup noises, in accordance with embodiments of the present invention.
Figure 2B:
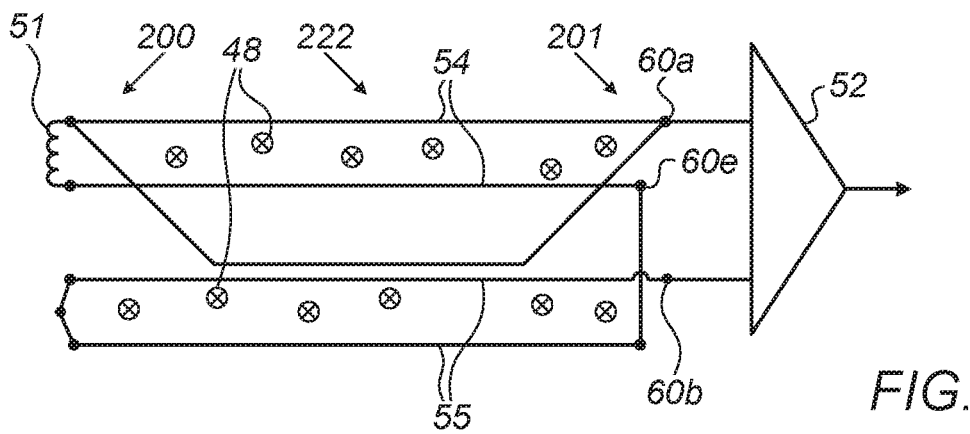

FIGS. 2A and 2B are schematic block diagrams of wiring assemblies 111 and 222 configured to cancel magnetic pickup noises, in accordance with embodiments of the present invention Each of the shown wiring configurations comprise two pairs of leads connected to each other in a way that cancels magnetic pickup noises.

In both embodiments shown in FIGS. 2A and 2B, a first lead pair 54 and a second lead pair 55, both of which can be viewed as a single winding coil, encompass a same area, up to a preset tolerance. Thus, ambient alternating magnetic field lines 48 induct very similar interfering signals in both lead pairs. Note that, in FIG. 2A, the crossing zones of lead pairs 55 encompass a very small area compared with the total area encompassed, and thus has a negligible effect on the values of inducted pickup signals.

As seen in FIG. 2A, lead pair 54 couples magnetic sensor 51 to electrical readout circuitry 52, essentially a single amplifier. The second pair of leads, lead pair 55, is connected in an inverse-parallel configuration to lead pair 54, between inputs 60a and 60b of the amplifier. The disclosed coupling is realized using a differential input port 100 at a first end of wiring assembly 111 and a differential output port 101 at a second end of wiring assembly 111, respectively.

At the second end, lead pair 55 is electrically shorted to the respective lead pair 54, at output points 60c and 60d of sensor 51. Thus, an interfering signal generated in lead pair 55 is essentially the same as the interfering signal generated in lead pair 54, but with inverse polarity. In this way, interfering signals (i.e., voltages) between inputs 60a and 60b are canceled out.

FIG. 2B shows an embodiment, in which second lead pairs 55 is connected, in series, to lead pair 54 at a point 60e, and the two pairs of leads form, in series, an interconnect between sensor 51 and inputs 60a and 60b of electrical readout circuitry 52. An interfering current inducted in lead pair 55 is essentially the same as the interfering current inducted in lead pair 54, but with inverse polarity, thus canceling out the opposing interfering currents, resulting in zero interfering signals between amplifier inputs 60a and 60b. The disclosed coupling is realized using a differential input port 200 at a first end of wiring assembly 222 and a differential output port 201 at a second end of wiring assembly 222, respectively.

The schematic diagrams shown in FIGS. 2A and 2B are chosen purely for the sake of conceptual clarity. The schematic geometrical schemes of connecting lead pairs aiming at achieving cancellation of interfering signals by encompassing a similar effective area is brought by way of example. Other designs are possible, for example, one comprising overlaying one pair of leads on top of the other. Various types of magnetic sensors may be used, such as sensors based on coils which utilize a Faraday effect, sensors based on micro-electro-mechanical devices that utilize a Lorentz force, and others.

Figure 3:
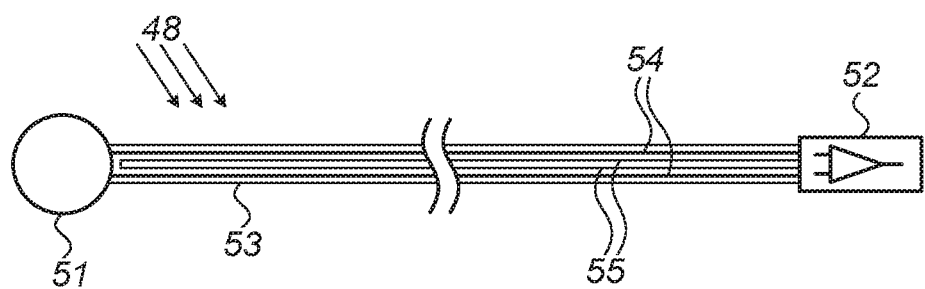
FIG. 3 is a schematic pictorial drawing of a wiring assembly implemented on a flexible printed circuit board (PCB), in accordance with embodiments of the present invention.

FIG. 3 is a schematic, pictorial drawing of wiring assembly implemented on a flexible printed circuit board (POB) 53, in accordance with embodiments of the present invention PCB 53 is patterned with two pairs of leads. A coil 51 of a magnetic sensor is connected to first patterned lead pair 54. As seen, both lead pair 54 and lead pair 55 encompass an area penetrated by ambient magnetic field lines 48. The second pair of leads (i.e., lead par 55) is patterned on PCB 53 such a way that lead pair 54 and lead pair 55 encompass a same area, up to a preset tolerance.

In an embodiment, electrical readout circuitry 52 is connected on PCB 53 to lead pairs 54 and 55 in an inverse-parallel configuration in order to receive signals from sensor 51 that are free of interference by magnetic pickup noises that may be otherwise generated by the two pairs of leads. In another embodiment, electrical readout circuitry 52 is connected on PCB 53 by an in-series configuration of lead pairs 54 and 55, that cancels out, at the input of electrical readout circuitry 52, magnetic pickup noises that may be generated by the two pairs of leads. In some embodiments, PCB 53 is fitted in a distal end of catheter 21 that is used for position tracking.

The example shown in FIG. 3 is chosen purely for the sake of conceptual clarity. In alternative embodiments, the arrangement, identity, and number of components patterned or placed on PCB 53 may vary. The shape of PCB 53 and of lead pairs 54 and 55 may be different, as will occur to a person skilled in the art. For example, the two pairs of leads can be patterned one on top of the other, with a patterned insulating layer between them to prevent shorting the two pairs of leads.

Figure 4A:
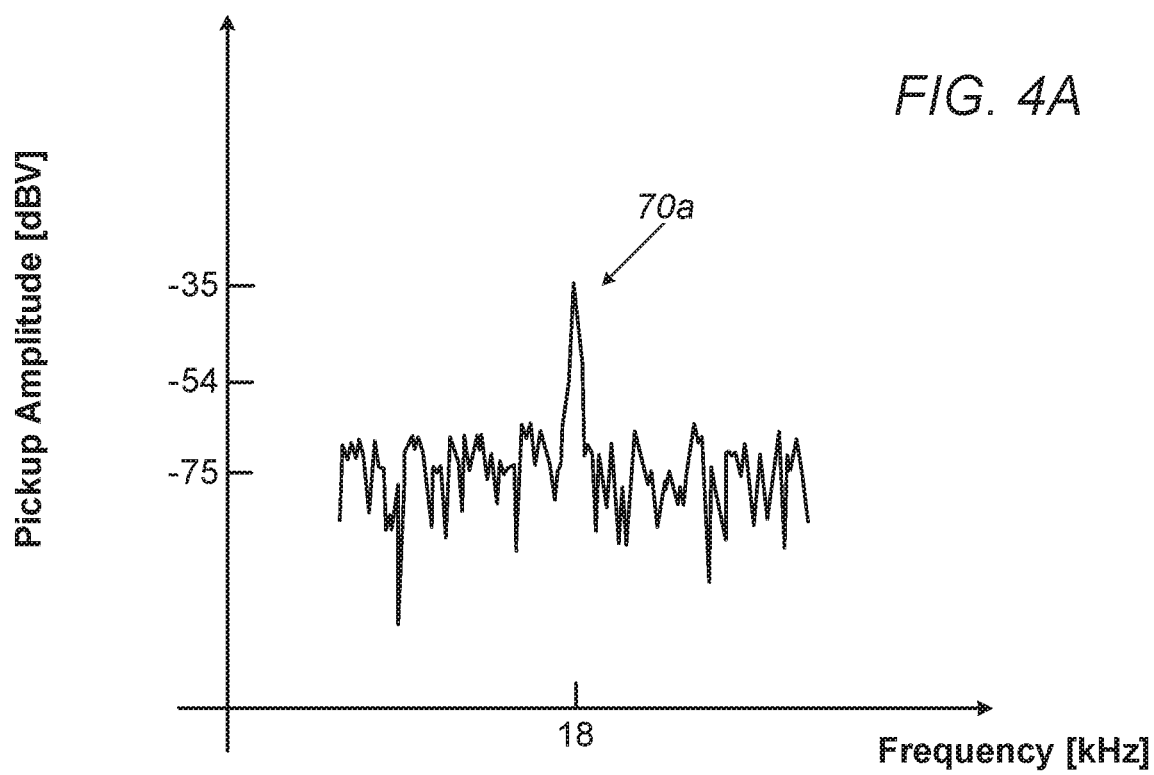
FIGS. 4A and 4B are graphs that compare magnetic pickup noise with and without noise cancelling wiring assembly, in accordance with the embodiment shown in FIG. 2A.
Figure 4B:
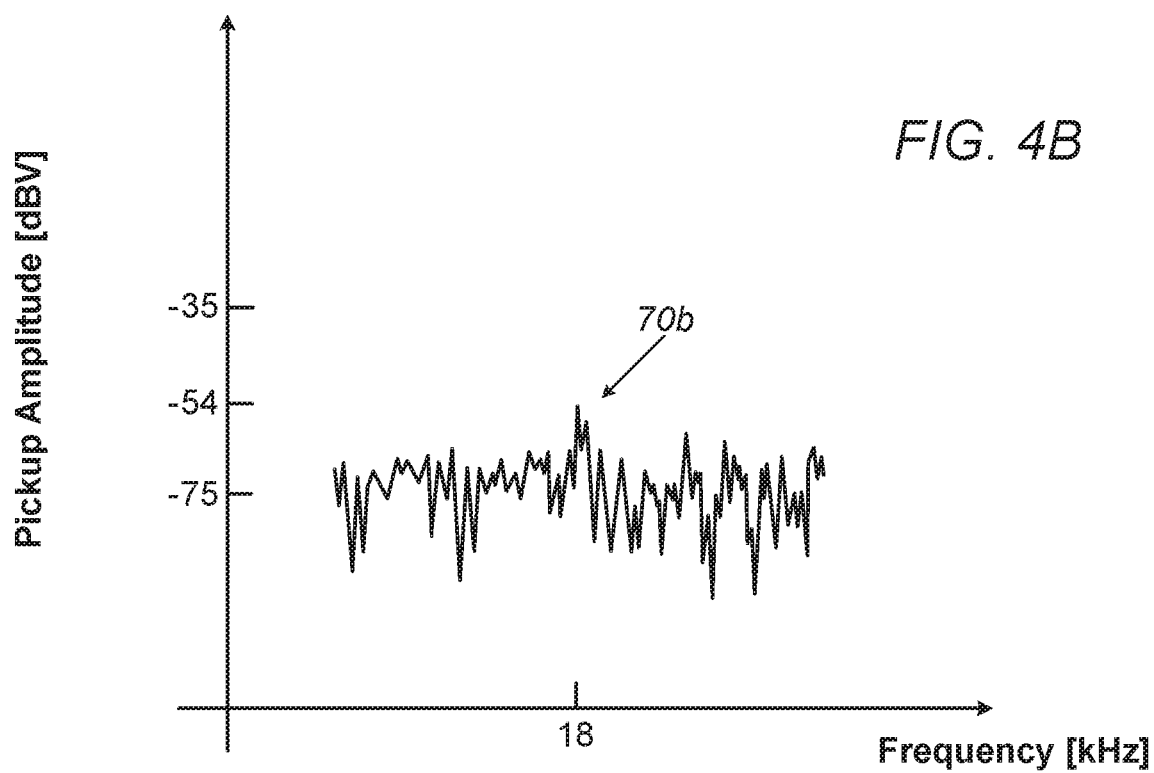

FIGS. 4A and 4B are graphs that compare magnetic pickup noise with and without noise cancelling wiring assembly, in accordance with the embodiment shown in FIG. 2A. Specifically, the figures show pickup noises without and with a second pair of leads connected in an inverse-parallel configuration to the first pair of pairs.

FIG. 4A shows a spectrum of input noise generated by lead pair 54. As seen, the input noise is mostly white noise. The pickup noise peak is seen at a frequency of about 18 kHz. As seen in FIG. 4A, when not compensated (e.g., by the embodiment seen in FIG. 2A), pickup noise amplitude 70a at 18 kHz has a value of −35 dBV about 40 dBV higher than the white noise. FIG. 4B shows a spectrum of input noise generated by lead pairs 54 and 55, which are connected in an inverse-parallel configuration with each other. FIG. 4B shows pickup noise amplitude 70b, which results from an inverse-parallel connection scheme. As seen, pickup noise amplitude 70b has a value of −54 dBV, which is about 20 dBV lower than the uncompensated pickup noise amplitude 70a.

The graphs shown in FIGS. 4A and 4B are brought, by way of example, to demonstrate empirically the pickup cancellation effect by an inverse-parallel connection scheme. Other measurements can be made, as well as other analysis methods applied, to demonstrate the efficacy of either one of the two connection schemes shown in FIGS. 2A and 2B.

Although the embodiments described herein mainly address cardiac catheters, the methods and systems described herein can also be used in other applications, such as in neurology and otolaryngology. In general, the methods and schemes described herein can also be used with any systems that utilize magnetic sensors, and in particular with navigation systems.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A wiring assembly, comprising:
    a differential input port, configured to receive a differential signal from, a sensor at a first end of the wiring assembly;
    a differential output port, configured to output the differential signal at a second end of the wiring assembly;
    a readout circuitry, which is coupled to receive the outputted differential signal at the second end of the wiring assembly; and
    first and second pairs of electrical leads, which convey the differential signal from the first end to the second end, and which are connected to one another at the first end and at the second end in a configuration that cancels pickup of an ambient magnetic field by the wiring assembly; and wherein the second pair of leads is connected in series to the first pair of leads.

2. The wiring assembly according to claim 1, wherein the first pair of leads and the second pair of leads encompass a same area, up to a preset tolerance.

3. The wiring assembly according to claim 1, wherein the second pair of leads is inverse-parallel connected to the first pair of leads.

4. The wiring assembly according to claim 1, wherein the first pair of leads and the second pair of leads are patterned on a flexible printed circuit board (PCB).

5. The wiring assembly according to claim 1, wherein the sensor comprises a magnetic sensor.

6. An assembly wiring method, comprising:
    providing a differential input port, configured to receive a differential signal from a sensor at a first end of a wiring assembly;
    providing a differential output port, configured to output the differential signal at a second end of the wiring assembly; providing a coupling readout circuitry to receive the outputted differential signal at the second end of the wiring assembly; and
    wiring a first pair of electrical leads and a second pair of electrical leads to create the wiring assembly, such that the first pair of leads and the second pair of leads are wired to each other in a configuration that cancels interfering signals picked up by the first and second pairs due to an ambient magnetic field; and wherein wiring the pairs of leads comprises connecting the second pair of leads in series to the first pair of leads.

7. The method according to claim 6, wherein wiring the pairs of leads comprises wiring the first pair of leads and the second pair of leads to encompass a same area, up to a preset tolerance.

8. The method according to claim 6, wherein wiring the pairs of leads comprises inverse-parallel connecting the second pair of leads to the first pair of leads.

9. The method according to claim 6, wherein wiring the pairs of leads comprises patterning the first pair of leads and the second pair of leads on a flexible printed circuit board (PCB).

10. The method according to claim 6, wherein the sensor comprises a magnetic sensor.

* * * * *